United States Patent [19]

Winston

[11] Patent Number: 5,496,568
[45] Date of Patent: Mar. 5, 1996

[54] FUNGAL DISEASE CONTROL IN CULTIVATED PLANTS

[75] Inventor: Anthony E. Winston, East Brunswick, N.J.

[73] Assignee: Church & Dwight Co., Inc., Princeton, N.J.

[21] Appl. No.: 494,523

[22] Filed: Jun. 26, 1995

[51] Int. Cl.$^6$ .......... A01N 43/28; A01N 37/02; A01N 37/06; A01N 59/00
[52] U.S. Cl. .......... 424/717; 424/715; 424/716; 514/383; 514/557; 514/558; 514/560; 514/709; 514/710; 514/711; 514/777; 514/778; 514/779; 514/780; 514/781; 514/782; 514/783; 514/784; 504/120; 504/123; 504/125; 71/DIG. 1
[58] Field of Search .......... 424/715, 716, 424/717; 504/120, 123, 125; 514/383, 557, 558, 560, 709, 710, 711, 777, 778, 779, 780, 781, 782, 783, 784; 71/DIG. 1

[56] References Cited

U.S. PATENT DOCUMENTS

| | | | |
|---|---|---|---|
| 4,599,233 | 7/1986 | Misato et al. | 424/717 |
| 5,330,964 | 7/1994 | Alesi, Jr. | 504/119 |
| 5,338,551 | 8/1994 | Lajoie | 424/717 |
| 5,342,630 | 8/1994 | Jones | 424/717 |

OTHER PUBLICATIONS

The Agrochemicals Handbook, 2d ed., Unwin Brothers Limited, Old Working (Surrey), 1987, p. A347/Aug. 1987.

Primary Examiner—Allen J. Robinson
Assistant Examiner—John D. Pak
Attorney, Agent, or Firm—Charles B. Barris

[57] ABSTRACT

The present invention provides an effective method for controlling foliage and root fungus infection in cultivated crops. A fungicide composition in the form of an aqueous formulation which is applied to pre-harvest crops contains ingredients such as propiconazole, sodium bicarbonate, potassium bicarbonate, sodium oleate, sodium caprylate and xanthan gum. The combination of sodium oleate, sodium caprylate and xanthan gum functions as an effective spreader-sticker medium for forming an adherent coating on plant foliage surfaces, and for saturating ground soil. The coating exhibits both immediate and long duration fungicidal activities.

21 Claims, No Drawings

FUNGAL DISEASE CONTROL IN CULTIVATED PLANTS

BACKGROUND OF THE INVENTION

The control of phytopathogenic fungi is of great economic importance since fungal growth on plants or on parts of plants inhibits production of foliage, fruit or seed, and the overall quality of a cultivated crop. About 25 percent of all fungal diseases in agriculture and horticulture are caused by powdery mildew phytopathogens.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain an inorganic bicarbonate and an optional carbonate compound. It is known that bicarbonate and carbonate compounds exhibit fungicidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillium italicum* and *Penicillium digitatum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

U.S. Pat. No. 4,599,233 describes a fungicide composition which consists of sodium bicarbonate in combination with a surface active food emulsifier such as sorbitan monostearate.

Japanese patent 53118523 describes the combination of sodium bicarbonate and lecithin as an active agent for the control of agricultural and fruit storage fungus diseases.

Japanese patent 56043207 describes a biocidal composition containing sodium bicarbonate and a polyglycerol fatty acid ester. The biocide controls *Penicillium digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

German patent DE 2927994 describes a fungicide which consists of sodium bicarbonate incorporated into a food-compatible surfactant such as saccharose laurate.

Japanese patent 57062208 describes horticultural fungicides in which the addition of sodium bicarbonate to polyoxin or thiophanatemethyl increases the fungicidal activity of the organic biocide against *Botrytis cinerea* on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wild, rice sheath blight, rice blast and citrus canker.

There remains a continuing need for improved methods for providing preventive and curative fungicidal activity for the protection of cultivated plants with a minimum of phytotoxic side effects.

Accordingly, it is an object of this invention to provide a bicarbonate salt-containing fungicide composition for controlling fungal diseases in cultivated plants.

It is another object of this invention to provide a method for controlling foliar-borne and soil-borne fungal diseases in agricultural and horticultural crops with an aqueous fungicide formulation having a synergistic combination of inorganic and organic fungicidal-active ingredients.

Other objects and advantages of the present invention shall become apparent from the accompanying description and examples.

DESCRIPTION OF THE INVENTION

One or more objects of the present invention are accomplished by the provision of a method for controlling fungal disease in cultivated plants which comprises contacting the plant matter with a fungicidally effective application of an aqueous formulation which has a content comprising (1) between about 0.1–2 weight percent of an ingredient selected from the group consisting of alkali metal and ammonium bicarbonates; (2) between about 0–1 weight percent of a basic ingredient selected from the group consisting of alkali metal and ammonium carbonates; (3) between about 0.05–2 weight percent of propiconazole; (4) between about 0.05–1 weight percent of a surfactant ingredient selected from the group consisting of alkali metal and ammonium $C_{12}$–$C_{22}$ aliphatic-containing carboxylate, sulfonate, sulfate and phosphate salts; (5) between about 0–0.25 weight percent of a hydrotrope ingredient selected from the group consisting of alkali metal and ammonium $C_7$–$C_{10}$ fatty acid salts; and (6) between about 0–0.5 weight percent of a hydrophilic polymer ingredient; based on the formulation weight.

In another embodiment this invention provides a fungicide composition which is a dry blend formulation comprising (1) between about 1–20 parts by weight of an ingredient selected from the group consisting of alkali metal and ammonium bicarbonates; (2) between about 0–10 parts by weight of an ingredient selected from the group consisting of alkali metal and ammonium carbonates; (3) between about 0.5–20 parts by weight of propiconazole; (4) between about 0.5–10 parts by weight of a surfactant ingredient selected from the group consisting of alkali metal and ammonium $C_{12}$–$C_{22}$ aliphatic-containing carboxylate, sulfonate, sulfate and phosphate salts; (5) between about 0–2.5 parts by weight of a hydrotrope ingredient selected from the group consisting of alkali metal and ammonium $C_7$–$C_{10}$ fatty acid salts; and (6) between about 0–5 parts by weight of a hydrophilic polymer ingredient.

The organic fungicide ingredient is a commercial product which corresponds to the structural formula:

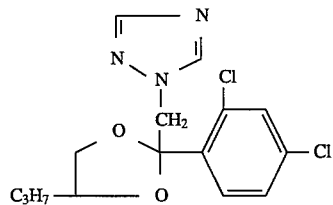

The compound is chemically identified as propiconazole, which is sold under tradenames such as BANNER (Ciba-Geigy). The formal nomenclature for the compound is 1-[[2-(2,4-dichlorophenyl) -4-propyl1,3-dioxolan-2-yl]methyl] -1-H-1,2,4-triazole.

The application of a present invention pesticide formulation to agricultural and horticultural plant-growth sites to combat fungi also is effective for eradication of insects such as aphids, mites, and the like.

An invention aqueous formulation can be prepared by pre-blending the solid ingredients, and then dispersing the blended admixture in an aqueous medium to a selected concentration of bicarbonate and propiconazole ingredients. Optionally, the ingredients can be individually dispersed in the aqueous medium.

An invention aqueous formulation can be prepared as a concentrated medium which is diluted further before usage, or the dilute aqueous formulation can be prepared directly by adding the individual ingredients or a pre-blend of ingredients to an aqueous medium.

An invention dilute aqueous fungicidal solution is in a ready-to-use form which can be applied directly to the foliage of plants, bushes and trees, such as by electrodynamic spraying techniques. An adherent film-like coating forms on the plant matter surfaces after the aqueous medium has evaporated. An invention formulation has particular advantages for controlling foliar-borne fungi by local systemic bioactivity.

The bicarbonate salt ingredient of an invention fungicide formulation is sodium bicarbonate, potassium bicarbonate or ammonium bicarbonate, or any mixture thereof.

Illustrative of a bicarbonate salt ingredient in a formulation are sodium, potassium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; and the like. Multiple bicarbonate salts are fungicidally more effective than a single bicarbonate salt, as illustrated in Example II.

The basic carbonate salt ingredient of an invention dilute aqueous fungicide formulation typically is between about 0.05–1 weight percent of sodium carbonate, potassium carbonate, ammonium carbonate or lithium carbonate, or any mixture thereof.

Multiple inorganic salt compounds can be utilized in a broad range of molar quantities relative to each other. In one aspect the molar quantity of a carbonate salt compound is determined by pH control considerations when aqueous formulations are prepared. The content of a carbonate salt compound can be varied to control the pH of an aqueous fungicide formulation at a desired level in the range of about 7.5–11. An aqueous fungicide formulation of the present invention tends to have a higher fungicidal activity at higher pH values.

The inclusion of a carbonate salt ingredient in an aqueous fungicide formulation is an important feature of the present invention method of controlling fungal disease in agricultural and horticultural plant life and plant soil. In addition to providing alkaline pH control, the carbonate salt potentiates the fungicidal activity of the bicarbonate salt ingredient. Further, under ambient atmospheric conditions, the carbonate salt in the adherent film-like coating on plant matter and soil particle surfaces reacts with carbon dioxide and moisture to form bicarbonate salt in situ over a prolonged duration.

The bicarbonate and carbonate salts are effective for rapid eradication of fungal infection, and are further potentiated by mixing with the propiconazole. However, due to their high solubility, the salts do not remain on the plant for long periods, e.g., more than about a week. They are removed by rain water or absorbed into the plant and are diluted and carried away in the plant's vascular system. The propiconazole provides longer term systemic protection against reinfection and protects new growth.

The surfactant ingredient of an invention fungicide formulation is an anionic surface active derivative selected from alkali metal and ammonium $C_{12}$–$C_{22}$ aliphatic-containing carboxylate, sulfonate, sulfate and phosphate salts. These anionic surfactants provide superior dispersant activity when an invention aqueous formulation is prepared.

An invention aqueous formulation is in the form of a stable aqueous dispersion which exhibits excellent spreader-sticker and film-forming properties when applied to plant foliage and soil.

Surfactants which provide suitable dispersant properties are anionic compounds such as alkyl sulfates and alkyl ether sulfates having 12–20 carbon atoms in the alkyl group. The ether sulfates can contain about 1–10 oxyethylene groups in the molecule. The sulfate surfactants can be in the form of sodium, potassium, ammonium, lower alkylamine or lower alkanolamine salts. Amine compounds are illustrated by dimethylamine, trimethylamine, diethanolamine, triethanolamine, and the like.

Other suitable anionic surfactants include sodium and potassium alkylbenzenesulfonates, in which the alkyl group contains about 9–15 carbon atoms; sodium alkyl glycerol ether sulfonates; sodium coconut oil fatty acid monoglyceride sulfates and sulfonates; sodium salts of sulfuric acid esters of oxyethylated fatty alcohols; sodium sulfosuccinate esters; condensation products of fatty acids with sarcosine; monoester or diester phosphates of $C_{12}$–$C_{18}$ fatty alcohols in the form of sodium, potassium or ammonium salts (e.g., Gafac PE-510, GAF Corporation); and the like. Anionic surfactants are described in references such as U.S. Pat. No. 4,528,039 and 5,037,818, incorporated herein by reference.

Other suitable anionic surfactants are $C_{12}$–$C_{22}$ fatty acid salts selected from alkali metal and ammonium salts of natural straight chain and synthetic branched chain fatty acids, which have a saturated or unsaturated structure. Illustrative of natural fatty acids are myristic acid, palmitic acid, stearic acid, oleic acid, linoleic acid, arachidic acid, behenic acid, cetoleic acid, and the like.

A $C_{12}$–$C_{22}$ fatty acid salt ingredient can consist of two or more saturated or unsaturated carboxylic acids such as those derived from beef and mutton tallow, lard, cottonseed oil, palm oil, and the like.

A preferred aspect of the present invention is the usage of the surfactant ingredient in combination with between about 0.01–0.25 weight percent of a hydrotropic ingredient in an invention aqueous fungicide formulation, or between about 0.1–2.5 parts by weight in an invention dry blend formulation. The term "hydrotrope" as employed herein refers to a straight-chain or branched-chain $C_7$–$C_{10}$ fatty acid salt which functions to stabilize and maintain the solubility of the surfactant ingredient in the aqueous medium, as the concentration of the bicarbonate salt-containing aqueous medium increases by water evaporation after application of the aqueous fungicide formulation to plant foliage. If the anionic surfactant is salted out of the aqueous solution, it is ineffective for spreading the bicarbonate salt and propiconazole ingredients for maximum coverage of fungus-infected plant foliage. The combination of the surfactant and hydrotrope ingredients promote the biocidal efficacy of the bicarbonate and propiconazole ingredients.

Suitable $C_7$–$C_{10}$ fatty acid hydrotrope compounds include sodium, potassium, ammonium, lower alkylamine and lower alkanolamine salts of enanthylic acid, caprylic acid, pelargonic acid, capric acid, and the like, or any mixture thereof.

Hydrotrope usage is described in publications such as U.S. Pat. No. 4,444,573; incorporated by reference.

The optional hydrophilic polymer ingredient of an invention fungicide formulation is selected from water-soluble organic polymers which exhibit pseudoplastic rheological properties in an aqueous medium. A preferred content of hydrophilic polymer in a dilute aqueous fungicide formulation is between about 0.01–0.4 weight percent. A preferred content of hydrophilic polymer in a dry blend formulation is between about 0.1–4 parts by weight.

The term "water-soluble" as employed herein refers to a hydrophilic polymer ingredient which has a solubility of at least about one gram per 100 grams of water at 25° C. The term "pseudoplastic" as employed herein refers to the rheological behavior of an aqueous solution containing a dissolved hydrophilic polymer ingredient, in which the apparent viscosity of the aqueous solution decreases with increasing shear rate.

Illustrative of water-soluble polymers which exhibit pseudoplastic properties in an aqueous medium are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, alkali metal salts of maleic anhydride copolymers, alkali metal salts of poly(meth)acrylate, and the like.

Many of the water-soluble polymers are large volume commercial products. Sodium carboxymethyl cellulose (CMC) is available in powder or granular form having a particle size of 50–200 microns. CMC is available in a degree of substitution (DS) range of 0.38–1.4.

One type of preferred aqueous formulation in accordance with the present invention is one containing two or more alkali metal or ammonium bicarbonates, alkali metal or ammonium carbonate, alkali metal or ammonium $C_{12}$–$C_{22}$ fatty acid salt, alkali metal or ammonium $C_7$–$C_{10}$ fatty acid salt, a hydrocolloid gum, and propiconazole.

The ingredients in an invention fungicide formulation can be selected to include nitrogen, phosphorus and potassium elements in a fertilizer-effective ratio and quantity that qualifies the composition to function as a fertilizer in addition to its function as a fungicide, when applied to cultivated crops. When an aqueous solution containing fertilizer elements is sprayed on plant foliage, there is direct absorption of the fertilizer elements into the leaves. A typical fertilizer ratio of NPK is 5–10–5.

Besides nitrogen, phosphorus and potassium, an invention fungicide fertilizer formulation can contain trace elements, and other essential elements as exemplified by sulfur as contained in a compound such as water-soluble sodium bisulfite or thiourea.

An invention fungicide formulation can include one or more other biologically active ingredients, such as those which exhibit herbicidal, insecticidal or plant growth regulating activity.

A fungicide formulation of the present invention has a novel combination of properties for the practice of pesticide control in agricultural and horticultural applications.

The bicarbonate and carbonate ingredients exhibit fungicidal properties, and the efficacy of the propiconazole ingredient is enhanced by the presence of bicarbonate and carbonate salts. A lesser quantity of organic pesticide ingredient can be employed to achieve a desired degree of pest control, as demonstrated in Example I of the present specification.

A present invention aqueous fungicide medium can be formulated to exhibit no phytotoxicity, or to minimize the toxic effects of salt stress on plants by the bicarbonate and carbonate ingredients.

The alkaline pH of a present invention fungicide formulation provides advantage for the control of infectious phytopathogenic fungi which thrive under acidic soil conditions, such as Rhizoctonia, Pythium and Fusarium species.

A significant feature of a preferred invention fungicide formulation is the presence of surfactant, hydrotrope and hydrophilic polymer ingredients, which function as a spreader-sticker medium when the fungicide formulation is applied to plant foliage as an aqueous solution. An applied aqueous solution forms an adherent coating of ingredients on plant foliage or fruit, and saturates the rooted soil. The surfactant ingredient aids in spreading and sticking the fungicide formulation ingredients to the foliage or fruit to which it is applied. The hydrotrope ingredient maintains the surface activity of the surfactant under application conditions. The hydrophilic polymer ingredient increases the amount of aqueous fungicide composition which adheres to the plant matter surfaces because of its static high apparent viscosity. During a spraying procedure, the hydrophilic polymer ingredient contributes a low mobile viscosity to the spray solution, which facilitates the spraying action. After spraying, the resultant solid coating resists drifting under wind conditions, and exhibits humectant properties in addition to enhanced fungicidal activity.

Another important advantage of an invention fungicide formulation derives from the water-solubility of contained inorganic salts and spreader-sticker ingredients. The filmlike coating of an invention fungicide formulation on plant matter surfaces can be removed readily by water-washing. Conventional fungicide formulations which contain a petroleum-based or fatty acid ester type spreader-sticker ingredient leave an oily residue on treated plant foliage or fruit which is difficult to remove.

A present invention fungicide formulation is adapted for broad spectrum application to field crops to prevent or eradicate fungal disease, or to inhibit re-infection by phytopathogenic fungi. Typically the aqueous formation is sprayed on a field crop at least twice during the growth cycle, with a time interval between about 5–20 days.

A present invention fungicide formulation has particular advantage for the control of fungal diseases such as *Botrytis cinerea* in crops such as ornamental stock, bedding plants, turf, cereals, vegetables, fruits, cotton, sugar cane, and the like.

Illustrative of particular crops are pre-harvest and post-harvest stages of grape, apple, pear, cucumber, potato, celery, rose, peanut, pecan, and the like.

A present invention fungicide formulation can be biocidally effective against *Diplocarpin rosae, Didymella bryoniae, Colletotrichum orbiculare, Botrytis cinerea, Penicillium digitatum, Guignardia bidwellii* and *Puccinia hordei.*

A present invention fungicide formulation also can be biocidally effective against powdery mildew species which include *Erysiphe asperifolium, Erysiphe betae, Erysiphe cichoracearum, Erysiphe cruciferarum, Erysiphe galeopsidis, Erysiphe graminis, Erysiphe pisi, Erysiphe polygoni, Erysiphe ranunculi, Erysiphe trifolii, Erysiphe verbasci, Microsphaera alphtoides, Oidium euonymi-japonicae, Oidium hortensiae, Podosphaera leucotricha, Podosphaera tridactyla, Sphaerotheca alchemillae, Sphaerotheca fuliginea, Sphaerotheca maculans, Sphaerotheca pannosa, Uncinula bicornis* and *Uncinula necator.*

A present invention fungicide formulation also can be biocidally effective against downy mildew species which include *Peronospora antirrhini, Peronospora arborescens, Peronospora destructor, Peronospora farinosa, Peronospora ficariae, Peronospora galligena, Peronospora grisea, Peronospora lamii, Peronospora parasitica, Peronospora sparsa, Peronospora trifoliorum, Peronospora viciae, Pseudoperonospora humuli,* and *Plasmopara vitacola.*

The following examples are further illustrative of the present invention. The components and specific ingredients are presented as being typical, and various modifications can be derived in view of the foregoing disclosure within the scope of the invention.

EXAMPLE I

This Example illustrates the synergistic fungicidal activity exhibited by a mixture of a bicarbonate salt and a commercial organic fungicide against foliar-borne fungus growth.

Leaflets, heavily infected with powdery mildew, are detached from greenhouse-grown Mary Devor cultivar roses. The stem end of the leaflet is placed in an open aluminum pan containing 2% water agar.

The leaflets are sprayed to run off with a solution of the test formulation. After 18–24 hours the quantity of powdery mildew remaining is scored as follows:

0=no mildew, 1=10% coverage, 2=30% coverage, 3=50% coverage, 4=70% coverage, 5=90+% coverage.

Each test formulation is evaluated twice using 10 replicates. The following formulations are compared:

|  | CONTROLS | | | INVENTION FORMULATIONS | | |
|---|---|---|---|---|---|---|
|  | A | B | C | 1 | 2 | 3 |
| propiconazole[1] | 0.390 | 0.000 | 0.000 | 0.130 | 0.100 | 0.180 |
| KHCO$_3$ | 0.000 | 0.500 | 0.000 | 0.340 | 0.000 | 0.000 |
| NaHCO$_3$ | 0.000 | 0.000 | 0.500 | 0.000 | 0.250 | 0.125 |
| Rhodopon OS[2] | 0.225 | 0.225 | 0.225 | 0.225 | 0.225 | 0.225 |
| water | 99.385 | 99.275 | 99.725 | 99.305 | 99.425 | 99.470 |

[1]BANNER; Ciba Geigy.
[2]Sodium oleyl sulfate; Rhone-Poulenc.

The following table is a summary of comparative data which demonstrate the fungicidal effectiveness of the Control and Invention Formulations under the test conditions.

TABLE

| Test Samples | Mean score | Std dev. | Sig.* |
|---|---|---|---|
| Water | 4.95 | 0.22 | c |
| Control A | 2.40 | 1.23 | b |
| Control B | 2.45 | 1.40 | b |
| Control C | 2.55 | 1.64 | b |
| Inv. Form. 1 | 1.60 | 0.69 | a |
| Inv. Form. 2 | 1.55 | 0.69 | a |
| Inv. Form. 3 | 1.70 | 0.87 | a |

*Products with different letters are significantly different (p, 0.05) based on Duncan's multiple range test.

The data demonstrate that both sodium bicarbonate and potassium bicarbonate provide synergistic fungicidal effects against powdery mildew when mixed with propiconazole. Thus, a mixture of one-fourth strength propiconazole with one-half strength sodium bicarbonate (Formulation 2) significantly outperforms both propiconazole (Control A) and sodium bicarbonate (Control C) used at full strength. Similarly, mixtures of about one-half strength propiconazole plus one-fourth strength sodium bicarbonate (Formulation 3), and of one-third propiconazole and two-thirds potassium bicarbonate (Formulation 1), outperform propiconazole, sodium bicarbonate and potassium bicarbonate (Control B) used at full strength.

The comparative data demonstrate the advantages which are obtained by the practice of the present invention embodiments for the control of fungal disease in agricultural and horticultural applications.

A present invention formulation provides a high level of fungicidal activity with a lower concentration of fungicide ingredients, which permits a lessening of any phytotoxic effects.

Due to the different modes of systemic activity of each fungicide ingredient in an invention formulation, there is a lesser probability that a fungus species will become resistant to the pesticide formulation.

Additionally, the lower concentration of fungicide ingredients in an invention pesticide formulation minimizes undesirable residues being released in the environment.

EXAMPLE II

This Example illustrates the preparation of a fungicide powder concentrate in accordance with the present invention.

A blend of the following ingredients is prepared:

|  | Parts |
|---|---|
| propiconazole | 10 |
| sodium bicarbonate | 43 |
| potassium bicarbonate | 22 |
| sodium oleate | 20 |
| sodium caprylate | 8 |

The formulated concentrated powder is diluted with water by the dispersion of 1 part of the powder blend into 100 parts of water. The resulting solution is sprayed onto a field crop of growing grape vines.

The formulation is effective for controlling Unicinula necator powdery mildew and Botrytis cinerea bunch rot infections. The aqueous formulation is applied four times to the grape vines with a 14 day interval.

The multiple bicarbonate salts are fungicidally more effective than an equivalent quantity of a single bicarbonate salt for control of the fungal diseases.

The blend is reformulated with the addition of four parts by weight of xanthan gum to enhance the spreader-sticker properties of the formulation for control of fungus infections in agriculture.

EXAMPLE III

This Example illustrates the preparation of a fungicide formulation in accordance with the present invention.

|  | Parts |
|---|---|
| propiconazole | 21 |
| potassium bicarbonate | 55 |
| sodium carbonate | 2 |
| potassium PFAD salt[1] | 15 |
| sodium caprate | 10 |
| sodium carboxymethyl- | 15 |

-continued

|  | Parts |
|---|---|
| cellulose[(2)] | |
| water | 50 |

[(1)]Palm fatty acid distillate.
[(2)]Aldrich Chemical Co., CMC of 3000–6000 centipoises, intrinsic viscosity of 2% aqueous solution at 25° C..

The solid ingredients are blended, and the blend is suspended in water to form an aqueous emulsion.

The emulsion formulation is diluted with water to 0.2% by weight of bicarbonate ingredient. The diluted formulation is effective as a fungicide for controlling *Podosphaera leucotricha* powdery mildew and apple scab infections in an orchard of apple trees during the fruiting season.

EXAMPLE IV

This Example illustrates the preparation of a concentrated aqueous fungicide formulation.

|  | Parts |
|---|---|
| propiconazole | 4.00 |
| potassium bicarbonate | 10.00 |
| sodium bicarbonate | 10.00 |
| potassium palmitate | 15.00 |
| sodium caprylate | 5.00 |
| guar gum | 2.00 |
| butylated hydroxytoluene (BHT) | 0.02 |
| water | 57.98 |

The aqueous concentrate is prepared by dissolving the potassium bicarbonate in the water, and then with stirring adding the other ingredients.

The prepared concentrated aqueous formulation is diluted 1 part to 40 parts of water. The diluted formulation is effective for prevention of foliar-borne fungal diseases on cultivated plants. The formulation inhibits propagation of *Sphaerotheca fuligenea* powdery mildew and *Colletotrichum orbiculare* anthracnose on cucurbits.

What is claimed is:

1. A method for controlling fungal disease in cultivated plants which comprises contacting the plant matter with a fungicidally effective application of an aqueous formulation which has a content comprising (1) between about 0.1–2 weight percent of an ingredient selected from the group consisting of alkali metal and ammonium bicarbonates; (2) between about 0–1 weight percent of a basic ingredient selected from the group consisting of alkali metal and ammonium carbonates; (3) between about 0.05–2 weight percent of propiconazole; (4) between about 0–1 weight percent of a surfactant ingredient; (5) between about 0–0.25 weight percent of a hydrotrope ingredient selected from the group consisting of alkali metal and ammonium $C_7$–$C_{10}$ fatty acid salts; and (6) between about 0–0.5 weight percent of a hydrophilic polymer ingredient; based on the formulation weight.

2. A method in accordance with claim 1 wherein the bicarbonate ingredient is sodium bicarbonate, potassium bicarbonate or ammonium bicarbonate, or any mixture thereof.

3. A method in accordance with claim 1 wherein the basic ingredient is between about 0.05–1 weight percent of sodium carbonate, potassium carbonate, ammonium carbonate or lithium carbonate, or any mixture thereof, and the pH of the formulation is in the range between about 7.5–11.

4. A method in accordance with claim 1 wherein the surfactant ingredient is between about 0.05–1 weight percent of a member selected from the group consisting of alkali metal and ammonium $C_{12}$–$C_{22}$ aliphatic-containing carboxylate, sulfonate, sulfate and phosphate salts.

5. A method in accordance with claim 1 wherein the surfactant ingredient is palmitic acid, stearic acid, oleic acid or palm fatty acid distillate salt or any mixture thereof.

6. A method in accordance with claim 1 wherein the surfactant ingredient is benzenesulfonate or sulfosuccinate salt or any mixture thereof.

7. A method in accordance with claim 1 wherein the surfactant ingredient is an oxyalkylene-containing sulfate salt.

8. A method in accordance with claim 1 wherein the hydrotrope ingredient is between about 0.01–0.25 weight percent of enanthylic acid, caprylic acid, pelargonic acid or capric acid salt or any mixture thereof.

9. A method in accordance with claim 1 wherein the hydrophilic polymer ingredient comprises between about 0.01–0.4 weight percent of a hydrocolloid gum.

10. A method in accordance with claim 1 wherein the hydrophilic polymer ingredient comprises between about 0.01–0.4 weight percent of a cellulosic derivative.

11. A method in accordance with claim 1 wherein the hydrophilic polymer ingredient comprises between about 0.01–0.4 weight percent of a starch derivative.

12. A method in accordance with claim 1 wherein the hydrophilic polymer ingredient comprises between about 0.01–0.4 weight percent of xanthan gum or guar gum.

13. A method in accordance with claim 1 wherein the cultivated plants are in a growth cycle and the aqueous formulation is applied to the plants at least twice with a time interval between about 5–20 days.

14. A method in accordance with claim 1 wherein the cultivated plants are one of a crop selected from the group consisting of peanut, cotton, sugar cane, fruits, vegetables, turf, and ornamentals.

15. A method in accordance with claim 1 wherein the disease being controlled is a foliar-borne.

16. A method in accordance with claim 1 wherein the disease being controlled is a Uncinula, Guignardia, Botrytis, Podosphaera or Phyllactinia fungus.

17. A method in accordance with claim 1 wherein the disease being controlled is a powdery mildew or downy mildew fungus.

18. A fungicide composition which is a dry blend formulation comprising (1) between about 1–20 parts by weight of an ingredient selected from the group consisting of alkali metal and ammonium bicarbonates; (2) between about 0–10 parts by weight of an ingredient selected from the group consisting of alkali metal and ammonium carbonates; (3) between about 0.5–20 parts by weight of propiconazole; (4) between about 0–10 parts by weight of a surfactant ingredient; (5) between about 0–2.5 parts by weight of a hydrotrope ingredient selected from the group consisting of alkali metal and ammonium $C_7$–$C_{10}$ fatty acid salts; and (6)

between about 0–5 parts by weight of a hydrophilic polymer ingredient.

19. A fungicide composition in accordance with claim 18 wherein the surfactant ingredient is between about 0.5–10 parts by weight of a member selected from the group consisting of alkali metal and ammonium $C_{12}$–$C_{22}$ aliphatic-containing carboxylate, sulfonate, sulfate and phosphate salts.

20. A fungicide composition in accordance with claim 18 which is a water-diluted formulation for fungicidally effective application to cultivated plants for systemic control of foliar-borne fungal disease.

21. A fungicide composition in accordance with claim 18 which has a fertilizer effective ratio and quantity of nitrogen, phosphorus and potassium elements.

* * * * *